US00PP18261P3

(12) United States Plant Patent
Chandler

(10) Patent No.: US PP18,261 P3
(45) Date of Patent: Dec. 4, 2007

(54) CARMINE STRAWBERRY PLANT

(50) Latin Name: *Fragaria×ananassa Duchesne*
Varietal Denomination: Carmine

(75) Inventor: Craig K. Chandler, Dover, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 144 days.

(21) Appl. No.: 10/613,317

(22) Filed: Jul. 7, 2003

(65) Prior Publication Data

US 2005/0010981 P1 Jan. 13, 2005

(51) Int. Cl.
*A01H 5/00* (2006.01)

(52) U.S. Cl. ..... Plt./208

(58) Field of Classification Search ..... Plt./208, Plt./209
See application file for complete search history.

(56) References Cited

PUBLICATIONS

Rondon et al.; Strawberry Cultivars Grown Under Protected Structure and Their Susceptibility to Natural Infestation of the Cotton Aphid, Aphis Gossypii Glover.; Hortscience 38(5): p. 806, Aug. 2003.(Abstract).*

* cited by examiner

*Primary Examiner*—Kent Bell

(57) ABSTRACT

This invention is a new and distinct variety of strawberry plant named 'Carmine'. 'Carmine' is characterized by high December through February production of fruit that are firm, deep red, glossy, and moderately resistant to *Botrytis* and Anthracnose fruit rot diseases when grown in west central Florida.

1 Drawing Sheet

Botanical designation: *Fragaria×ananassa* Duchesne.
Cultivar designation: 'Carmine'.

BACKGROUND OF THE INVENTION

All phases of the development of the new variety took place at Dover, Fla. as part of an ongoing breeding program. 'Carmine' resulted from a controlled cross between 'Rosa Linda' (U.S. Plant Pat. No. 9,866) and FL 93-53 (not patented). Seeds from the cross were germinated in a greenhouse, and the resulting seedlings were planted and allowed to produce daughter plants by asexual propagation (i.e. by runners). Two daughter plants from each seedling were transplanted to raised beds, where they fruited during the 1995–96 season. 'Carmine' (as represented by two daughter plants from the original seedling) exhibited attractive, firm fruit, and therefore was selected for further evaluation. 'Carmine' has been asexually propagated by runners, annually, and further test plantings have established that the vegetative and fruit characteristics of the propagules are identical to the initial two daughter plants.

SUMMARY OF THE INVENTION

The invention is a new and distinct variety of strawberry named 'Carmine'. When 'Carmine' is grown in a subtropical fall and winter climate, it is set apart from all other strawberry varieties know to the inventor by a combination of the following characteristics: high December through February production (greater than 17,000 pounds of marketable fruit per acre); fruit that are firm, deep red, and glossy; and moderate resistance to *Botrytis* and anthracnose fruit rot diseases.

BRIEF DESCRIPTION OF THE DRAWING

FIG. 1 shows a typical plant of 'Carmine' during late February at Dover, Fla.

FIG. 2 shows typical fruit of 'Carmine' harvested at Dover, Fla. during the peak of the season.

DETAILED BOTANICAL DESCRIPTION

The following botanical description is that of mature plants of 'Carmine' grown under the ecological conditions (warm days, cool nights) prevailing at Dover, Fla. in late February. Colors are described using the Pantone® Color Formula Guide. Contrast is made to 'Sweet Charlie' (U.S. Plant Pat. No. 8,729) and 'Camarosa' (U.S. Plant Pat. No. 8,708), standard varieties, for reliable description. 'Carmine' is a promising candidate for commercial success in that it has high early season fruit production like 'Sweet Charlie', but has significantly firmer fruit than 'Sweet Charlie'. 'Carmine' is a short day cultivar. It has a more compact plant habit than 'Camarosa' and 'Rosa Linda'. Average height and width for mature plants is 19 cm and 26 cm respectively. Average petiole length and diameter is 15.6 cm and 2.5 mm respectively, and petioles have a medium pubescence. Terminal leaflets are essentially round, with an average length and breadth of 60 and 59 mm respectively, while secondary leaflets are very slightly ovoid, with an average length and breadth of 56 and 52 mm respectively. Leaflet apices and bases are obtuse. Leaflet margins are crenate and average 18 serrations per terminal leaflet, and 18 per secondary leaflet. The upper leaf surface is a dark grey green (Pantone® 370 U); the lower leaf surface is a light grey green (Pantone® 377 U); and the petiole is a medium yellow green (Pantone® 397 U). Flowers open at or above the canopy, and have an average of 5 petals and 24 stamens. Petals are round, with an average length and width of 9 mm. They have an entire margin and an obtuse apex and base. The average diameter of the corolla is 28 mm. The color of the calyx is yellow green (Pantone® 363 U). Pedicels attached to mature primary fruit are 11 to 22 cm long, 2.0 mm in diameter, yellow green (Pantone® 384), with branching of the inflorescence usually occurring very close to the crown. Mean fruit weight is less than or similar to that of 'Sweet Charlie' (Table 1 and 2) and 'Rosa Linda'. Primary fruit are medium conic or wedge shaped (weighing 25–35 g); whereas secondary and tertiary fruit are mostly short conic (weighing 10–25 g). The external color of fully mature fruit is deep red (Pantone® 1807C) and glossy; internal color is a warm red (Pantone® 1795C). The achenes are generally greenish yellow and level with or slightly protruding from the fruit surface. The calyx is generally medium in size, attractive, and composed of 12 mostly elliptic sepals, which are about 10 mm in length and 4–6 mm in width. Some of the sepals have two or more incisions at their apex. Fruit of 'Carmine' are firmer than those of 'Sweet Charlie' (Table 3) and 'Rosa Linda'. The flavor of this fruit is acceptable, but not as highly regarded as that of 'Camarosa', 'Sweet Charlie', and 'Strawberry Festival' (U.S. Plant Pat. No. 14,739) (Table 4). While generally sweet and juicy, the fruit, at times, can be slightly astringent. The preferred planting date for 'Carmine' is October 10 to October 17. Early season yields of 'Carmine' compared favorably to 'Sweet Charlie' and 'Earlibrite' (U.S. Plant Pat. No. 13,061) during both the 1997–98 and 2001–02 seasons (Table 1 and 2). The December yield of 'Carmine' in 2001 was over twice that of 'Sweet Charlie'. Yield during December can be important to a Florida grower's profitability. The average price per flat (10.25 lbs) during the five seasons between 1995 and 2000 was $17.38, $11.57, $10.51, and $7.27 for December, January, February, and March respectively (Florida Agricultural Statistics Service). 'Carmine' is moderately resistant to the two most serious disease problems on strawberry in Florida: *Botrytis* fruit rot (caused by *Botrytis cinerea* Pers.exFr.) and anthracnose fruit rot (caused by *Colletotrichum acutatum* Simmonds). In an unsprayed trial during the 2001–02 and 2002–03 seasons, 7.3 and 2.2% of the 'Carmine' fruit harvested from February 19 to March 15 showed symptoms of *Botrytis* fruit rot, compared to 18.7 and 6.8% for 'Sweet Charlie', the susceptible control. In another unsprayed trial during the 2001–02 and 2002–03 seasons, 9.6 and 9.3% of the 'Carmine' fruit harvested from February 19 to March 22 showed symptoms of anthracnose fruit rot, compared to 28.9 and 47.0% for 'Strawberry Festival', the susceptible control. The susceptibility of 'Carmine' to the twospotted spider mite (*Tetranychus urtricae* Koch) is unknown, but a serious infestation has not yet been observed in research center or commercial trials. DNA banding patterns for 'Carmine', 'Sweet Charlie', 'Camarosa', 'Earlibrite', 'Oso Grande' (U.S. Plant Pat. No. 6,578) and 'Strawberry Festival' are presented in Table 5.

TABLE 1

Performance of strawberry cultivars at Dover, Fla. during the 1997-98 season[z].

| | Marketable yield (g/plant) | | | | | |
|---|---|---|---|---|---|---|
| Cultivar | December | January | February | March | Total | Wt/fruit[y] (g) |
| Carmine | 114 a[x] | 85 a | 246 ab | 212 b | 657 b | 16.4 c |
| Camarosa | 50 b | 105 a | 167 c | 426 a | 748 ab | 20.0 a |
| S. Charlie | 91 a | 54 b | 219 abc | 257 b | 622 b | 17.6 b |
| Earlibrite | 66 b | 110 a | 189 bc | 280 b | 645 b | 20.7 a |
| S. Festival | 58 b | 108 a | 255 a | 426 a | 847 a | 17.6 a |

[z]Transplants were obtained from the following nursery locations: 'Camarosa' from a commercial nursery in North Carolina; all other entries were from GCREC-Dover. 'Camarosa' was planted on 16 Oct.; all other cultivars were planted on 9 Oct.
[y]Mean fruit weight was determined by dividing total marketable fruit yield per plot by total marketable fruit number per plot.

TABLE 1-continued

Performance of strawberry cultivars at Dover, Fla. during the 1997-98 season[z].

| | Marketable yield (g/plant) | | | | | |
|---|---|---|---|---|---|---|
| Cultivar | December | January | February | March | Total | Wt/fruit[y] (g) |

[x]Within columns, means followed by one or more of the same letters are not statistically different for each other at P ≦ 0.05.

TABLE 2

Performance of strawberry cultivars at Dover, Fla. during the 2001-02 season[z].

| | Marketable yield (g/plant) | | | | |
|---|---|---|---|---|---|
| Cultivar | December | January | February | Total | Wt/fruit[y] (g) |
| Carmine | 232 a[x] | 62 b | 204 a | 499 a | 17.0 b |
| S. Charlie | 102 c | 92 a | 166 a | 360 b | 16.4 b |
| Earlibrite | 205 ab | 33 c | 201 a | 439 a | 21.1 a |
| S. Festival | 163 b | 61 b | 221 a | 444 a | 17.2 b |

[z]All transplants were obtained from a commercial nursery in North Carolina, and planted on 9 Oct.
[y]Mean fruit weight was determined by dividing total marketable fruit yield per plot by total marketable fruit number per plot.
[x]Within columns, means followed by one or more of the same letters are not statistically different for each other at P ≦ 0.05.

TABLE 3

Physical and chemical characteristics of strawberry fruit harvested at Dover, Fla. 23 Feb. 1998 and 25 Feb. 2002.

| | L value[z] | | Firmness (kg force) | |
|---|---|---|---|---|
| Cultivar | 1998 | 2002 | 1998 | 2002 |
| Carmine | 30.5 c[y] | 35.7 b | 0.38 a | 0.41 a |
| Camarosa | 29.6 c | 34.2 b | 0.43 a | 0.27 b |
| Sweet Charlie | 35.1 a | 38.2 a | 0.22 b | 0.30 b |
| S. Festival | 32.6 b | 35.6 b | 0.38 a | 0.42 a |

| | Soluble solids (%) | | Titratable acidity (% citric acid) | |
|---|---|---|---|---|
| Cultivar | 1998 | 2002 | 1998 | 2002 |
| Carmine | 8.6 | 6.5 | 0.77 | 0.86 |
| Camarosa | 7.7 | 8.5 | 0.87 | 0.93 |
| Sweet Charlie | 8.0 | 7.3 | 0.65 | 0.75 |
| S. Festival | 7.7 | 8.0 | 0.77 | 0.84 |

[z]The lower the value, the darker the color.
[y]Within columns, means followed by one or more of the same letters are not statistically different for each other at P ≦ 0.05.

TABLE 4

Sensory characteristics of strawberry fruit harvested at Dover, Fla. 25 Feb. 2002[z].

| Cultivar | Appearance | Firmness | Flavor | Sweetness |
|---|---|---|---|---|
| Carmine | 7.2 a[y] | 7.1 b | 5.3 c | 4.8 c |
| Camarosa | 6.7 b | 7.0 bc | 6.8 a | 6.6 a |
| Sweet Charlie | 6.2 b | 6.6 c | 6.2 b | 6.0 b |
| S. Festival | 7.5 a | 7.5 a | 7.2 a | 6.8 a |

[z]Means based on the rating of 72 untrained panelists. Characteristics are rated on a 1-9 hedonic scale, with 1 = dislike extremely, 5 = neither like nor dislike, and 9 = like extremely.
[y]Within columns, means followed by one or more of the same letters are not statistically different for each other at P ≦ 0.05.

TABLE 5

| | DNA marker analysis[z] | | | | |
|---|---|---|---|---|---|
| | Primer | | | | |
| | B06 | B07 | B14 | X11 | X06 |
| | Band number for each primer and DNA pattern | | | | |
| Variety | 123 | 1234 | 12345 | 1 | 12 |
| Carmine | 000 | 1101 | 00000 | 0 | 10 |
| Earlibrite | 101 | 1101 | 00000 | 0 | 11 |
| Sweet Charlie | 011 | 0101 | 00111 | 1 | 01 |
| Camarosa | 101 | 1010 | 00010 | 1 | 11 |
| Oso Grande | 001 | 1011 | 11010 | 1 | 10 |
| S. Festival | 000 | 1001 | 00010 | 1 | 10 |

[z]Random amplified polymorphic DNA (RAPD) patterns were determined using primers B06, B07, B14, X06, and X11 from Operon Technologies, Inc.. Stolon tip DNA's were isolated using DNeasy Plant ™ extraction kit from Qiagen ®, Inc. Amplification reactions were performed in 20 microliter volumes using a procedure adapted from Williams et al., 1990), Nucleic Acids Research 25:6531-6535. The reagents and conditions included 50 mM Tris (pH 8.3), 0.25 mg/mL bovine serum albumin, 2.1 mM $MgCl_2$, 0.5% Ficoll 400, 1.0 mM tartrazine, 0.2 mM each of dATP, dCTP, dGtp, dTTP, 1.0 mM primer DNA, 0.065 ng strawberry DNA, 1 unit Taq-DNA polymerase (Promega, Inc.). The reaction conditions were 4 minutes at 94° C., then 10 seconds at 94° C., 1 minute at 45° C., 3.5 minutes at 68° C., then 9 cycles of 10 seconds at 94° C., 1 minutes at 45° C. with an incrementation of 0.5 degrees per cycle, 3.5 minutes at 68° C., then 29 cycles of 10 seconds at 94° C., 1 minute at 40° C. and 3.5 minutes at 68° C. with a 10 second extension per cycle. The reactions were incubated in Model PTC-100 thermocycler (MJR, Inc.). The reaction products were analyzed with gel electrophoresis using 1.0% agarose 3:1 high resolution blend (AMRESCO, Inc.) in a running buffer of 0.045 M Tris-Borate, 0.001 M EDTA. The separated DNA was detected using ethidium bromide and viewed with a ultra violet transilluminator. Reproducible polmorphic banding from the electrophoresis analysis was observed with the DNA primers. The amplification reactions resulted with varying levels of polymorphism, from 2 to 5 polymorphic bands depending on the primer used. The polymorphic bands were scored as 0 equals absence and 1 equals presence.

It is claimed:

1. A new and distinct variety of Strawberry plant, substantially as shown and described.

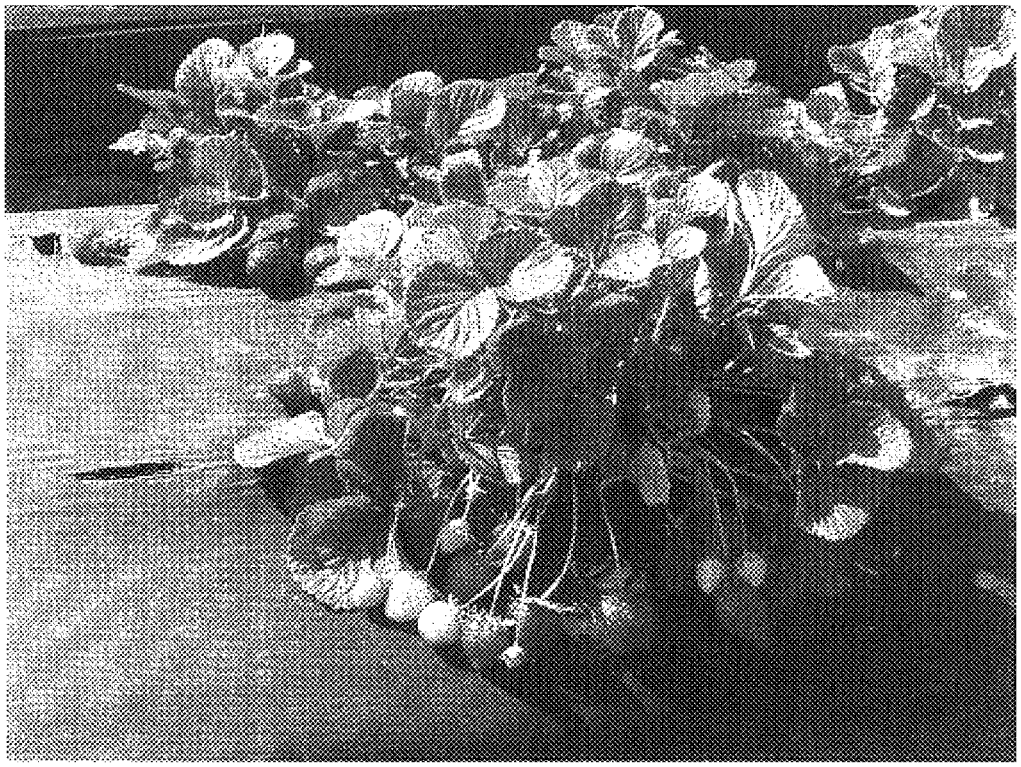
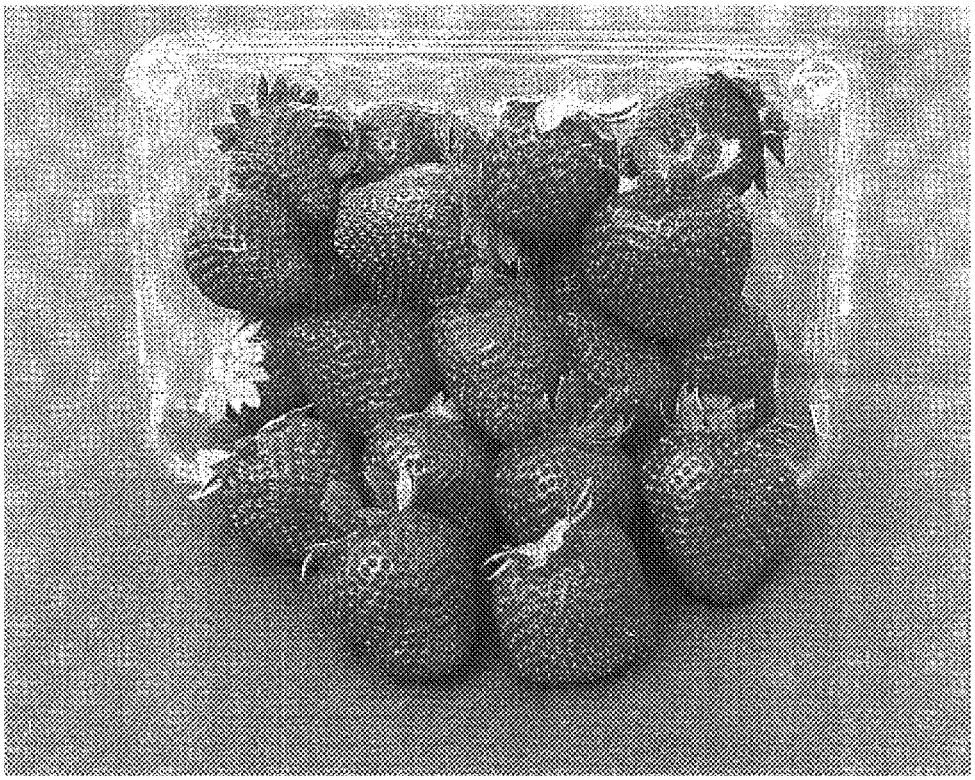

* * * * *